United States Patent [19]
Walker

[11] Patent Number: 5,139,420
[45] Date of Patent: Aug. 18, 1992

[54] DENTAL MIRROR SYSTEM
[76] Inventor: William S. Walker, 1229 E. D Ave., Kalamazoo, Mich. 49004
[21] Appl. No.: 578,588
[22] Filed: Sep. 4, 1990
[51] Int. Cl.⁵ .............................................. A61C 1/00
[52] U.S. Cl. ....................................................... 433/31
[58] Field of Search ................................ 433/29, 30, 31

[56] References Cited
U.S. PATENT DOCUMENTS

| 1,660,870 | 2/1928 | Fust | 433/31 |
| 2,720,702 | 10/1955 | Freedman | 433/31 |
| 3,014,279 | 12/1961 | Fosdal | 433/30 |
| 3,032,879 | 5/1962 | Lafitte | 433/30 |
| 3,592,199 | 7/1971 | Ostensen | 128/11 |
| 4,925,391 | 5/1990 | Berlin | 433/31 |

FOREIGN PATENT DOCUMENTS 1932912  1/1971  Fed. Rep. of Germany ........ 433/30

Primary Examiner—Cary E. O'Connor
Attorney, Agent, or Firm—Dressler, Goldsmith, Shore, Sutker & Milnamow, Ltd.

[57] ABSTRACT

The present invention is directed to a dental mirror system having a fluid conduit to provide a stream of fluid across the surface of the mirror to remove material from the mirror surface. The dental mirror system can also be provided with a light-transmitting cable to illuminate the work area and/or a suction conduit to remove material from the mouth of the patient.

1 Claim, 2 Drawing Sheets

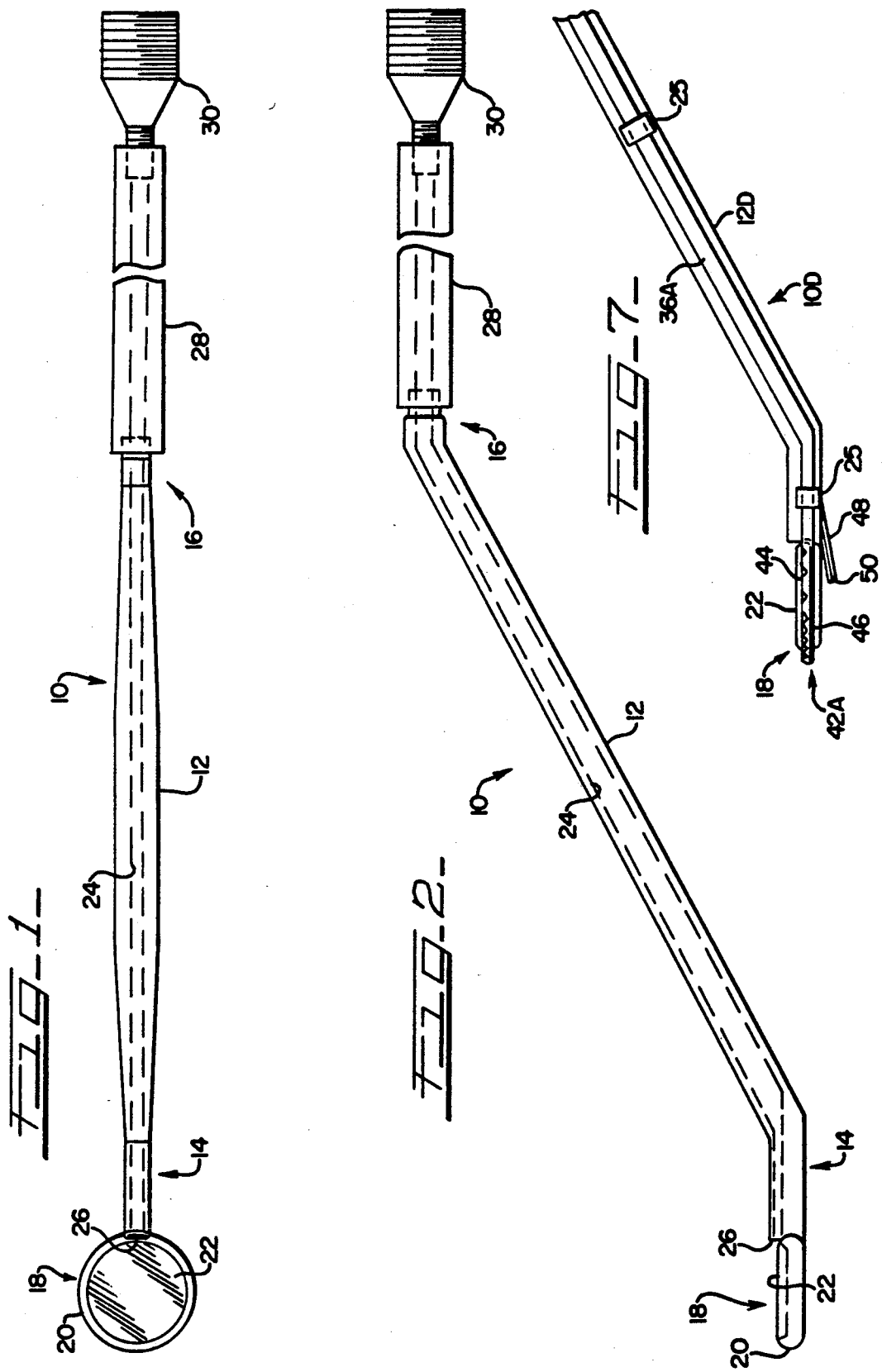

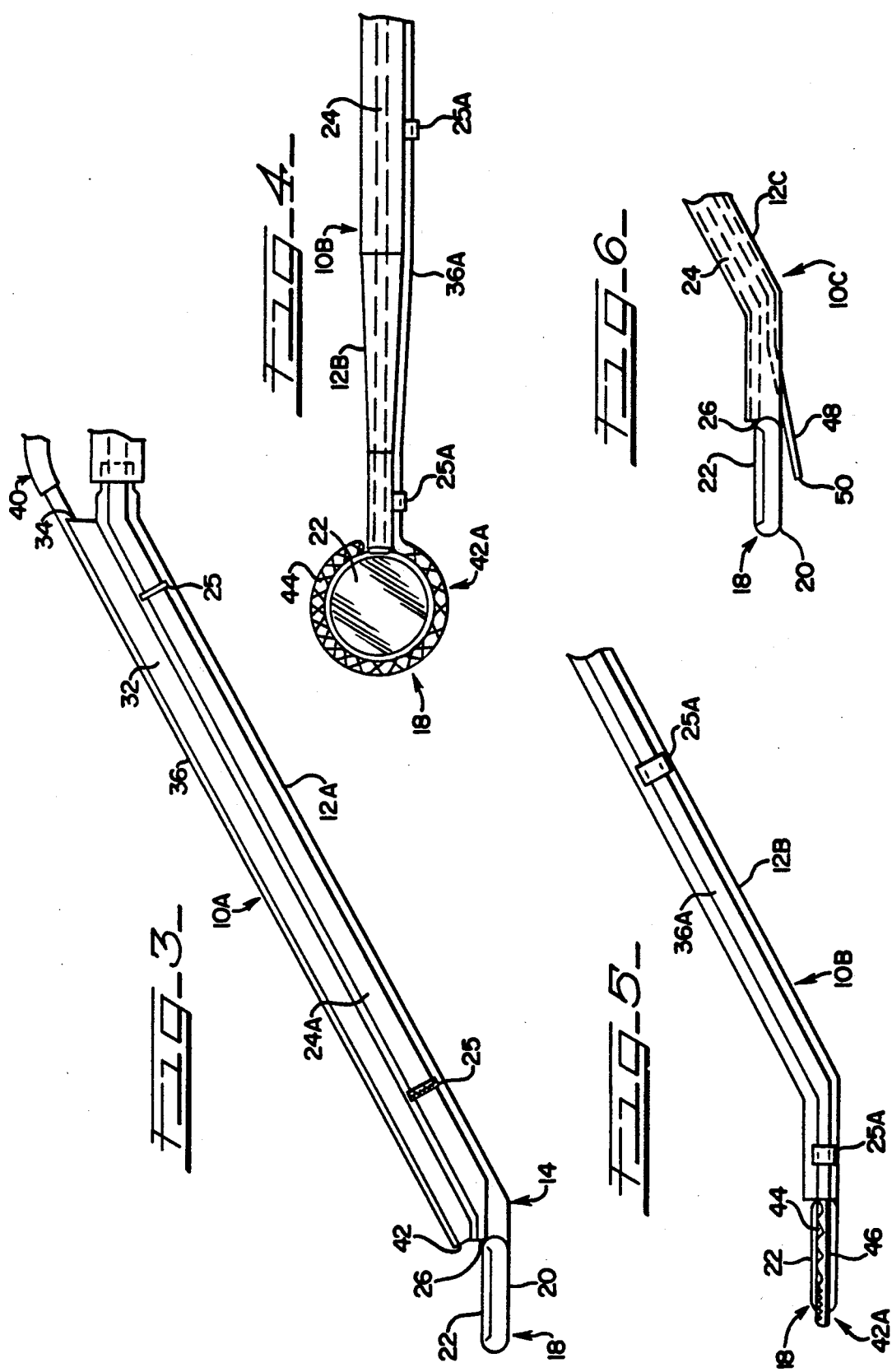

DENTAL MIRROR SYSTEM

TECHNICAL FIELD

This invention relates to dental mirrors and, in particular, to a dental mirror system that includes a mirror and a fluid conduit that provides a fluid stream across the mirror while the dental mirror system is in the mouth of a patient.

BACKGROUND OF THE INVENTION

Dental mirrors are utilized to permit a dentist to view obscure work areas within the mouth of a patient with minimum discomfort to the patient.

During dental procedures, e.g., drilling, scaling, and the like, particulate and/or fluid materials are often deposited upon the reflective surface of the mirror thereby interfering with the view of the work area. This interference can result in an improper performance of the procedure which can be harmful to the patient.

Dental mirrors are currently cleared of the materials by removing the mirror from the patient's mouth and wiping or rinsing the mirror. Requiring the removal of the mirror from the mouth is undesirable because a dentist must stop working, lose sight of the work area and relocate the work area before continuing to work, all of which increase the time required to treat the patient and thereby increase the length of time the patient suffers.

A powerful, distant light source positioned behind the dentist is often utilized to provide adequate lighting to the work area. The dentist must maneuver to prevent the shadow from being cast upon the work area. Also, the light undesirably shines into the eyes of the patient.

Materials that accumulate in the mouth during dental procedures are often removed by spitting them out or sectioning them off. Spitting out of the materials interrupts the work. Sectioning off the materials requires the placement of a dedicated tube in the mouth which can already be crowded with other dental instruments.

Accordingly, it is desirable to provide a dental mirror system that would improve the view of the work area by clearing materials from the reflective surface of the mirror without requiring the mirror be removed from the patient's mouth and possibly also provide a local light source and/or fluid removal capability.

SUMMARY OF THE INVENTION

The present invention provides a dental mirror system having an elongated arm, a mirror secured to a distal end of the arm, and a fluid conduit that terminates in an orifice adjacent to a reflective surface of the mirror to provide a fluid stream across the reflective surface. The fluid conduit can be defined by the arm or can be distinct therefrom.

As the dentist works in the mouth, foreign material collects on the reflective surface of the mirror and interferes with the view of the work area. This material is removed from the surface by providing a fluid stream across the reflective surface from the conduit and the orifice. The fluid can be a liquid, e.g., water, a gas, e.g., air, or, preferably, a combination of a liquid followed by a gas that removes the liquid from the reflective surface. Preferably, the fluid stream is activated by a foot control, but it can be activated by a control on the arm.

The dentist can work more efficiently because the dental mirror system cleans the reflective surface without requiring the mirror be removed from the mouth.

In another preferred embodiment, the arm provides a mounting for a light-transmitting cable having its light-emitting end adjacent to the reflective surface. The light-transmitting cable provides a local light source with the light-emitting end guiding light in a direction incident to the reflective surface whereby the light is reflected by the reflective surface onto the work area. Alternatively, the light-emitting end is adjacent to at least a section of the perimeter of the reflective surface and emits light along the length of the light-emitting end to illuminate the work area.

In yet another preferred embodiment, the dental mirror system includes a suction conduit for removal of material from the mouth without requiring the dentist to stop working or use a dedicated suction tube.

Numerous other advantages and features of the present invention will become readily apparent from the following detailed description of the invention, the accompanying drawings and the appended claims.

BRIEF DESCRIPTION OF THE DRAWINGS

FIG. 1 is a top elevational view of the dental mirror system showing the fluid conduit in phantom;

FIG. 2 is a side elevational view of the dental mirror system of FIG. 1;

FIG. 3 is a side elevational view of an alternative embodiment of the dental mirror system including a light-transmitting cable;

FIG. 4 is a top elevational view of an alternative embodiment of the dental mirror system including an alternative light-transmitting cable;

FIG. 5 is a side elevational view of the dental mirror system of FIG. 4;

FIG. 6 is a side elevational view of an alternative embodiment of the dental mirror system including a suction conduit; and, FIG. 7 is a side elevational view of an alternative embodiment of the dental mirror system including a light-transmitting cable and a suction conduit.

DETAILED DESCRIPTION

Although this invention is susceptible to embodiment in many different forms, there is shown in the drawings and will be described in detail, preferred embodiments of the invention. It should be understood, however, that the present disclosure is to be considered as an exemplification of the principles of the invention and is not intended to limit the invention to the embodiments illustrated.

Referring to FIGS. 1 and 2, the dental mirror system 10 comprises an elongated arm 12 having a distal end 14 and a proximal end 16, a mirror 18 affixed to the distal end 14, the mirror 18 having a mirror body 20 and a reflective surface 22, and a fluid conduit 24 that terminates in an orifice 26 positioned adjacent to the reflective surface 22. The fluid conduit 24 is connected to a fluid source (not shown) as by a tube 28 and a tube coupler 30.

The mirror body 20 is conventional secured to the distal end 14 as by welding, soldering, riveting, utilizing an adhesive, or the like.

The fluid conduit 24 is illustrated as being defined by the arm 12 which is the preferred embodiment.

FIG. 3 illustrates an alternative embodiment of the dental mirror system 10A wherein the fluid conduit 24A is not defined by the arm 12A. The fluid conduit 24A is illustrated as being secured to the arm 12A as by mounting brackets 25.

FIG. 3 also shows the arm 12A having a mounting ridge 32 extending substantially along the entire length thereof. The mounting ridge 32 has a mounting channel 34 in which a light-transmitting cable 36 is slidably received. The light-transmitting cable 36 has a distal light-emitting end 42 adjacent to the reflective surface 22 and a proximal end 40 connected to a light source (not shown).

The light-transmitting cable 36 provides a local light source to illuminate the viewing field of the mirror that at least includes the work area. Light is directed through the light-emitting end 42 incident to the reflective surface 22 which reflects the light onto the work area. Sliding the light-transmitting cable 36 along the mounting ridge 32 permits illumination of different work areas without moving the dental mirror system 10A.

FIGS. 4 and 5 illustrate an alternative embodiment of the dental mirror system 10B wherein the light-transmitting cable 36A is secured to the side of the arm 12B by mounting brackets 25A. The light-emitting end 42A is adjacent to at least a section of the perimeter of the reflective surface 22. The light-emitting end 42A has a light diffuser 44 that directs light through the upper surface of the light-emitting end 42 onto the work area. The light diffuser can be score marks on the upper surface of the light-emitting end 42A.

Preferably, the light diffuser 44 provides a substantially uniform emission of light along the length of the light-emitting end 42. To achieve this substantially uniform emission of light, the density of the light diffuser 44 increases along the length of the light-emitting end 42 as the distance from the light source increases. That is, the density of the scoring increases as the distance from the light source increases.

The lower surface of the light-emitting end 42A can also have a reflective coating 46 to redirect light that is incident thereto through the light diffuser 44.

FIG. 6 illustrates an alternative embodiment of the dental mirror system 10C further comprising a suction conduit 48 that defines an opening 50. In this embodiment, the opening 50 is positioned adjacent to a surface of the mirror body 20 opposed to the reflective surface 22. The suction conduit 48 extends into the arm 12C and is connected to a suction pump (not shown) that provides the desired suction.

Alternatively, the placement of the opening 50 with respect to the mirror 18 and of the suction conduit 48 with respect to the arm 12 can be conventionally varied. These alternative embodiments are not illustrated.

FIG. 7 illustrates an alternative embodiment of the dental mirror system 10D that includes both the light-transmitting cable 36A and the suction conduit 48.

In use, the dentist holds the dental mirror system 10 much as a conventional dental mirror is held. When the view of the work area is interfered with by particulate or fluid material on the reflective surface 22, the dentist activates the fluid stream to remove the material.

When the dental mirror system 10 includes a localized light source, the work area can be illuminated utilizing the local light source.

When the dental mirror system 10 includes the suction conduit 48, material can be removed from the mouth of the patient by activating the suction.

Switches for controlling the operation of the fluid source, the light source, and the suction pump are conventional and therefore are not shown. These switches are preferably located on a foot control switch but can be located on the arm of the dental mirror system for control by the hand.

This invention has been described in terms of specific embodiments set forth in detail. It should be understood, however, that these embodiments are presented by way of illustration only, and that the invention is not necessarily limited thereto. Modifications and variations within the spirit and scope of the claims that follow will be readily apparent from this disclosure as those skilled in the art will appreciate.

I claim:

1. A dental mirror system comprising:
    (a) an elongated arm defining an axis and having a distal end;
    (b) a mirror angularly secured to the distal end and having a reflective surface, associated with a viewing field, disposed at an obtuse angle relative to the axis of said elongated arm;
    (c) a fluid conduit extending along the length of said elongated arm and defining an orifice adjacent to the reflective surface of the mirror to provide a fluid stream across the reflective surface;
    (d) a light-transmitting cable extending along the length of said elongated arm in parallel relationship to said fluid conduit and having light-transmitting means adjacent to the reflective surface of the mirror and disposed to guide light in a direction incident to the reflective surface to illuminate the viewing field; and
    (e) a suction conduit extending along the length of said elongated arm in substantially parallel relationship to said fluid conduit and said light-transmitting cable, said suction conduit defining a suction opening adjacent to a surface of said mirror opposed to the reflective surface thereof so that activation of suction through said suction conduit can remove material from the mouth of a patient;
    said light-transmitting cable being slidingly received by said elongated arm and having said light-transmitting means adjacent to the reflective surface of the mirror.

* * * * *